(12) United States Patent
Schwarz et al.

(10) Patent No.: US 8,668,138 B1
(45) Date of Patent: Mar. 11, 2014

(54) SYSTEM AND METHOD FOR INPUTTING MEDICAL INFORMATION

(71) Applicants: Brian K. Schwarz, Lake in the Hills, IL (US); Raymond J. Bender, Elgin, IL (US)

(72) Inventors: Brian K. Schwarz, Lake in the Hills, IL (US); Raymond J. Bender, Elgin, IL (US)

(73) Assignee: Lattice Incorporated, Wheaton, IL (US)

( * ) Notice: Subject to any disclaimer, the term of this patent is extended or adjusted under 35 U.S.C. 154(b) by 0 days.

(21) Appl. No.: 13/771,971

(22) Filed: Feb. 20, 2013

Related U.S. Application Data

(60) Provisional application No. 61/731,208, filed on Nov. 29, 2012.

(51) Int. Cl.
*G06F 17/00* (2006.01)

(52) U.S. Cl.
USPC .......................... 235/375; 235/487; 235/462.1

(58) Field of Classification Search
USPC ................ 235/375, 487, 494, 462.01, 462.1, 235/462.07, 498
See application file for complete search history.

(56) References Cited

U.S. PATENT DOCUMENTS

| | | | |
|---|---|---|---|
| 2006/0278717 A1* | 12/2006 | VonKlinggraeff et al. | ... 235/487 |
| 2007/0067141 A1* | 3/2007 | Beshears et al. | .............. 702/173 |
| 2008/0121688 A1* | 5/2008 | Harrop | .......................... 235/375 |
| 2008/0223941 A1* | 9/2008 | Mrowiec | ....................... 235/494 |
| 2011/0026081 A1* | 2/2011 | Hamada et al. | .............. 358/1.18 |

* cited by examiner

*Primary Examiner* — Edwyn Labaze
(74) *Attorney, Agent, or Firm* — Barnes & Thornburg LLP; Erin J. Fox

(57) ABSTRACT

A method of inputting medical information comprises the step of printing a two-dimensional barcode from a first system, wherein the two-dimensional barcode comprises embedded data to input into a second system and wherein the data is separated by embedded key strokes that emulate entry of data into a user interface associated with the second system. The method further includes the steps of scanning the two-dimensional barcode utilizing a scanner associated with the second system and entering the embedded data into the user interface of the second system.

19 Claims, 7 Drawing Sheets

0930<tab>116292<tab><tab><tab><tab>S<tab>C<enter>

FIG. 9

SYSTEM AND METHOD FOR INPUTTING MEDICAL INFORMATION

CROSS-REFERENCE

This application claims the benefit of U.S. Provisional Patent Application No. 61/731,208, filed on Nov. 29, 2012, and entitled "System and Method for Inputting Medical Information," the entire disclosure of which is incorporated herein.

BACKGROUND

1. Field of the Disclosure

The present disclosure relates to systems and methods for inputting medical data and, more particularly, to systems and methods for automatically inputting medical information into a target system.

2. Description of the Background

During a doctor visit or a hospital stay, patients are oftentimes required to leave a sample of urine, blood, stool, or other biological samples for analysis. In addition, in outpatient or inpatient scenarios, caregivers, such as doctors, nurses, or other healthcare professionals, may collect tissue, fluid, a foreign body, a tumor, or other pathology specimen(s) for analysis. Whether a biological or a pathology specimen is collected, specific procedures must be followed to properly track the specimen as belonging to a particular patient. Many current systems for tracking specimens are time consuming and error-prone.

A prior art manual system 20 for tracking or inputting data relating to specimens is depicted in FIG. 1. In the system 20, one or more labels 53 (see FIG. 6) are printed out (at block 22), at a bed of a patient, in a doctor's office, in an in-home setting, at a nursing station, in a hospital laboratory, or in any other medical facility or location. The label(s) 53 is printed with a linear barcode representing a unique identifier for that specimen and the label(s) 53 is placed on a container for holding the specimen. The unique identifier, which is embodied in a linear barcode, is utilized for identification and tracking purposes as the specimen proceeds through collection, receiving, and resulting processes. A caregiver collects the specimen in the form of blood, urine, stool, swap, or other biological or pathology specimen at block 24. The caregiver writes missing data on the label at block 26, which is indicated by reference numeral 64 in FIG. 6, wherein the missing data may include a collection date, a collection time, a collector identifier for identifying the person who collected the specimen, a unique blood bank identifier, patient demographic data, and/or written notes that a nurse, phlebotomist, or other caregiver may write or print on the label.

Still referring to FIG. 1, when a container holding a specimen is received in the laboratory, a medical professional scans the linear barcode representing the unique identifier or accession number to identify the specimen in the system at block 28. Subsequent to scanning of the linear barcode, laboratories generally manually enter data that was physically written on the label(s) 53, as indicated by reference numeral 64, during the collection phase of block 26.

One label 53 created by the manual system 20 of FIG. 1 is depicted in FIG. 6. The label 53 includes type-written data 60, which may be for example, patient demographic data, such as a date of birth, a first name, a middle name, a last name, directions, and any other data. The label 53 may also include handwritten data 64 if further processing is required that includes notes not supported by the laboratory or pathology information system that generates the label 53. The label 53 further includes a linear barcode 62, as discussed above, that includes an encoded unique identifier or accession number. The label 53 contains the accession number, container identifier, or barcode number, which is used as a primary identifier for tracking and processing purposes in later laboratory or pathology analysis and reporting.

A further prior art electronic system 50, as seen in FIG. 2, utilizes an electronic transfer of data over a network to replace the step of manually entering data described above with respect to FIG. 1. In the electronic system 50, a caregiver collects blood, urine, stool, swap, or other biological or pathology specimen at block 52. The caregiver then prints a label 21 (see FIG. 5) for that specimen at block 54, wherein the label 21 includes type-written data 30 and a linear barcode 32 representing a unique identifier or accession number to uniquely identify that specimen. Once the barcode is scanned by a target system, for example a laboratory information system, pathology information system, electronic health record, or other healthcare system, and the unique identifier or accession number of the linear barcode 32 is recognized, the target system communicates at block 56 via a TCP/IP network connection utilizing the HL7 protocol with the electronic system 50 to communicate HL7 data over the network to update or input into the target system. The HL7 data contains, for example, the collection time, the collection date, and the collector identifier. At block 58, the target system automatically inputs the collection date, the collection time, and the collector identifier using the information electronically transferred from the electronic system 50.

While the prior art systems function in their intended manner, such prior art systems also have their drawbacks. For example, the manual entry of the manual system 20 is error-prone and time consuming. In addition, in relation to the electronic system 50, the target systems must be configured to send and receive information from the electronic system 50, which is not always the case. In some situations, there is no network interface available to the target system or it is cost-prohibitive to utilize an available network interface and, therefore, the manual system 20 must be utilized.

SUMMARY

In an illustrative embodiment a method of inputting medical information comprises the step of printing a two-dimensional barcode from a first system, wherein the two-dimensional barcode comprises embedded data to input into a second system and wherein the data is separated by embedded key strokes that emulate entry of data into a user interface associated with the second system. The method further includes the steps of scanning the two-dimensional barcode utilizing a scanner associated with the second system and entering the embedded data into the user interface of the second system.

In another illustrative embodiment, a method of inputting medical information comprises the step of printing a linear barcode from a first system, wherein the linear barcode comprises a unique identifier for an item to be tracked. The method further includes the step of printing a two-dimensional barcode from the first system, wherein the two-dimensional barcode comprises embedded data to input into a second system and wherein the data is separated by embedded key strokes that emulate entry of data into a user interface associated with the second system and further wherein the embedded data comprises information related to the item to be tracked. The method still further includes the steps of scanning the linear barcode utilizing a scanner associated with the second system, scanning the two-dimensional barcode utilizing the scanner associated with the second system, and entering the embedded data into the user interface of the second system.

In a further illustrative embodiment, a system for inputting medical information comprises a user device associated with a first system, wherein the user device is configured to accept data, and a printer associated with the user device for printing a linear barcode comprising a unique identifier for an item to be tracked and a two-dimensional barcode. The two-dimensional barcode comprises embedded data to input into a second system, wherein the data is separated by embedded key strokes that emulate entry of data into a user interface associated with the second system and further wherein the embedded data comprises information related to the item to be tracked. The system further includes a second system including a scanner for scanning the linear and two-dimensional barcodes and populating information associated with the linear and two-dimensional barcodes into the user interface associated with the second system.

BRIEF DESCRIPTION OF THE DRAWINGS

FIG. 9 is an illustrative set of instructions encoded within a two-dimensional barcode that is scanned during performance of the method steps of FIG. 4.

Other aspects and advantages of the present disclosure will become apparent upon consideration of the following detailed description, wherein similar structures have like or similar reference numerals.

DETAILED DESCRIPTION

The present disclosure is directed to systems and methods for inputting medical information into a target system. While the systems and methods of the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 3:
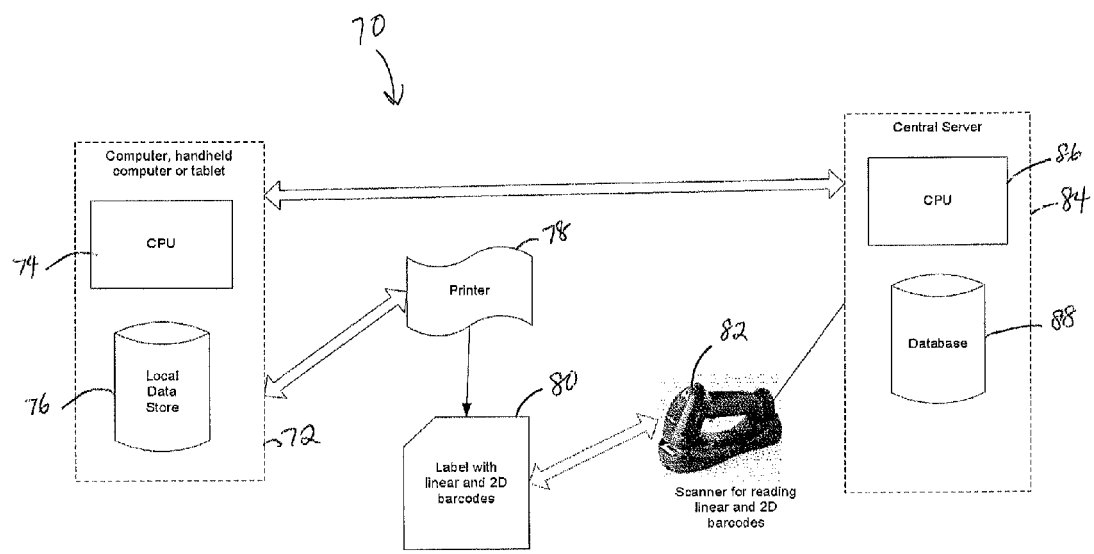
FIG. 3 is a schematic diagram of a system for implementing method steps taken during specimen collection and inputting specimen information into a target system.

A method 100 for specimen collection and inputting specimen information into a target system after specimen collection is shown is depicted in FIG. 3. A target system may be a laboratory information system, pathology information system, electronic health record, or any other healthcare system.

The method 100 is implemented by a system within a server, computer, handheld computer, tablet, or other user device, and may include any number of electronic components, such as a central processing unit, a monitor, a printer, or any other computer hardware or software and/or may include any number of user interfaces for accessing the system. Data within the system may be stored within a database and accessed in any suitable manner. While the methods 100 for operating the system may be disclosed herein as running on a central processing unit, the system may be accessed through an Internet website accessible from any location. In such embodiment, the Internet website may include any number of different security features.

One illustrative system 70 for implementing the methods 100 is depicted in FIG. 3. The system 70, one or more computers, handheld computers, tablets, other user devices, and combinations thereof (indicated by reference numeral 72) are utilized to input data related to specimen(s). The user device(s) 72 include a central processing unit 74 and a local data store or database 76 for storing data related to specimens and/or other data. The user device 72 has a wired or wireless connection to a printer 78, which prints a label 80 including a linear barcode and a two-dimensional barcode, as discussed in greater detail below. Optionally or additionally, one or more of the user devices 72 may be connected to any other suitable peripheral devices, for example, a camera, a video camera, scanner, plotter, microphone, or any other suitable peripheral device. A scanner 82 is utilized to read the linear and two-dimensional barcodes on the label 80. The scanner 82 may be wirelessly or otherwise connected to a central server 84, which includes a central processing unit 86 and a database 88. Optionally, the central server 84 may include any other alternative or additional components. The central server 84 may be located near the scanner 82 or remote from the scanner 82, for example, in another room or an offsite location. Once the barcodes are scanned, the appropriate data is saved in the database 88.

Figure 4:
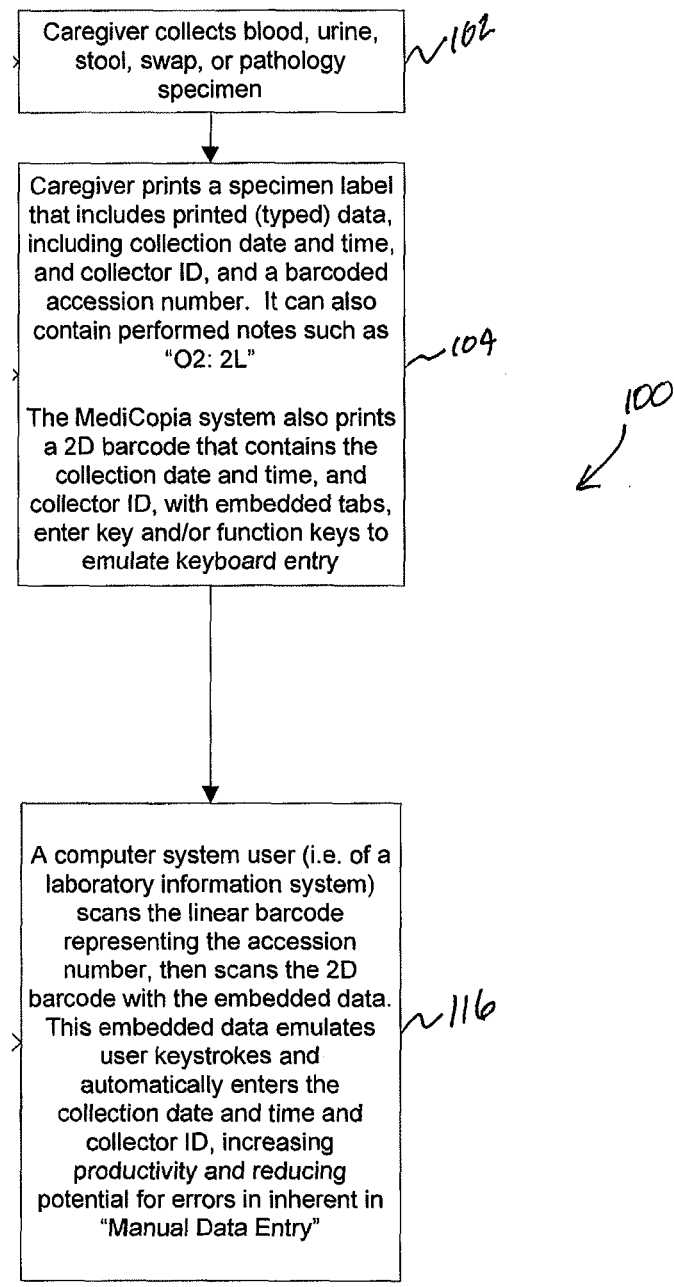
FIG. 4 is a flow diagram depicting the method steps taken during operation of the system of FIG. 3.
Figure 5:
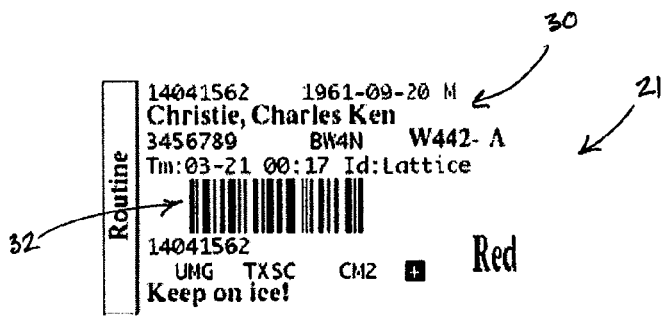
FIG. 5 is a sample label for a specimen collected in the electronic prior art system of FIG. 2.
Figure 6:
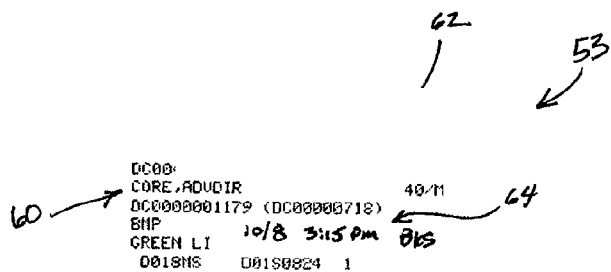
FIG. 6 is a sample label for a specimen collected in the manual prior art system of FIG. 1.

The method of FIG. 4 is at least partially implemented by the networked system 70, as seen in FIG. 3, which enables communication between one or more user device(s) 72, and the central server 84. The system 122 may include any number of user device(s) 72, which may be, for example, a computer, a handheld computer, a tablet, or any other suitable user device. The system 70 may include any number of user device(s) 72 connected through a wired data network and/or a wireless data network to each other and/or the central server 84. The wired data network may be a global network, a wide area network, or a local area network. The wireless data network, which may be coupled to the wired data network, may include one or more wireless data networks, such as cellular networks, WiFi networks, Bluetooth networks, etc. The user device(s) 72 and/or the central server 84 may be coupled to both the wired data network and the wireless data network through a network communication device within the user device 72 and a network communication device within the central server 84. In an illustrative embodiment, the user device(s) 72 may couple to the wired data network over wired connections and to the wireless data network over wireless links. In this manner, the user device(s) 72 may access the central server 84 through the wired data network and/or the wireless data network.

Referring to FIG. 3, each user device 72 may include a graphical user interface (not shown) and a computer portion. The graphical user interface may include one or more input/output (I/O) devices, such as a touch screen, a keyboard, a stylus, a joystick, or any other suitable I/O device, which can be arranged in various manners and have different shapes or designs. The touch screen may be a liquid crystal display (LCD), a display screen, a plasma screen, a light emitting diode (LED), or any other screen capable of displaying text and/or images and/or allowing input of text. The computer portion may also include an I/O device, the central processing unit (CPU) 74 (i.e., a microprocessor), memory (not shown), and a local data store or database 76. The CPU 74 may be any computer-processing unit, including multi-processor or single processor configurations. The memory may include, without limitation, any one or a combination of volatile memory elements (e.g., random access memory (RAM, such as DRAM, SRAM, SDRAM, etc.)) and nonvolatile memory elements (e.g., ROM, hard drive, tape, CDROM, etc.). The memory may incorporate electronic, magnetic, optical, and/or other types of storage media, and may have a distributed architecture where various components are situated remote form one another, but may still be accessed by the CPU 74, such as cloud computing. The graphical user interface is coupled to the I/O device such that commands or data entered by a user through the graphical user interface will be forwarded to the I/O device, to the CPU 74, and then to the memory.

Similarly, the CPU 86 within the central server 84 may be any computer-processing unit, including multi-processor or single processor configurations. The central server 84 may also include memory that may include, without limitation, any one or a combination of volatile memory elements (e.g., random access memory (RAM, such as DRAM, SRAM, SDRAM, etc.)) and nonvolatile memory elements (e.g., ROM, hard drive, tape, CDROM, etc.). The memory may incorporate electronic, magnetic, optical, and/or other types of storage media, and may have a distributed architecture where various components are situated remote form one another, but may still be accessed by the CPU 86, such as cloud computing.

The method as depicted in FIG. 4 may be in the form of one or more executable programs stored within the memory that are run within the CPU 74 and/or 86 (or other hardware device) or may be accessed through an Internet website accessible from any location. If an Internet website is utilized, the Internet website may include any number of different security features. The one or more executable programs, if run within the CPU 74 and/or 86, may be implemented in software, firmware, hardware, or a combination thereof. The databases 76 and/or 86 may store data related to specimens and/or any other data.

The method of FIG. 4 may be embodied in any computer-readable medium for use by or in connection with an instruction execution system, apparatus, or device, such as a computer-based system, processor-containing system, or other system that may fetch the instructions from the instruction execution system, apparatus, or device and execute the instructions. In the context of this application, a "computer-readable medium" may be any means that may store, communicate, propagate, or transport the program for use by or in connection with the instruction execution system, apparatus, or device. The computer readable medium may be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), a portable compact disc read-only memory (CDROM) (optical), and a portable USB storage device. In an illustrative embodiment, where the method is implemented in hardware, it should be obvious that it may also be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

While various components of the system 70 are disclosed, the system 70 may include any number of the depicted or additional electronic components, such as central processing units, monitors, printers, other peripheral device, and/or any other computer hardware or software.

Figure 7:
FIG. 7 is a sample label for a specimen collected in the system of FIG. 3.

At block 102 of FIG. 4, a caregiver, such as a nurse, doctor, phlebotomist, or any other healthcare provider, collects a specimen from a patient. The specimen may be blood, urine, stool, swap, or any biological or pathology specimen. Either before or after the specimen is collected, the caregiver prints one or more labels 106 (as seen in FIG. 7) for the particular specimen. The label 106 includes type-written data 108, for example, a date of birth, a first name, a middle name, a last name, directions, and any other suitable data. The label 106 further includes a linear barcode representing a unique identifier or accession number 110, which provides a unique identifier for each specimen container and acts as a primary identifier for tracking and processing purposes in later laboratory or pathology analysis and reporting. The label 106 may further include type-written notes 112, such as storage instructions, care instructions, or any other notes. A two-dimensional barcode 114 is either printed on the label 106 or as a separate label and may include the collection date, collection time, collector identifier, and/or any other suitable data or information. The two-dimensional barcode 114 further includes embedded key strokes, for example, tabs, characters, numbers, spaces, enter keys, function keys, or any other key strokes that emulate entry of data into a user interface or other source.

In an illustrative embodiment, the two-dimensional barcode 114 is a PDF-417 stacked linear barcode. The label(s) 106 may be placed along a height of the specimen container such that the barcode 114 does not curve around the container, thereby allowing the barcode 114 to be easily read by a scanner and allowing the content of the label(s) 106 to be easily read by the human eye. Optionally, the label(s) 106 may be placed on the specimen container in any other suitable manner.

Referring again to FIG. 4, after the label(s) 106 has been printed, the label(s) 106 is attached to a container for holding the specimen and the specimen is routed to a particular destination, for example, a laboratory, a hospital, or any other suitable healthcare site. In an illustrative example, the destination for the container holding the specimen is a laboratory. Once the specimen in its container with attached label(s) 106 arrives at the laboratory, an individual performing intake of the container with specimen, utilizes a user device, such as a computer, handheld computer, tablet, or other user device, to access the electronic system of the target system to input the data on the label(s) 106. In particular, at block 116, the individual utilizes a scanner that is embodied within the user device or is connected (either physically or wirelessly) to the user device and/or the electronic system to scan the linear barcode 110 on the label(s) 106. Once the linear barcode 110 is read, the electronic system pulls up a user interface with information including the unique identifier or accession number and any data associated with that accession number.

The individual thereafter scans the two-dimensional barcode 114 with the embedded data. Once the two-dimensional barcode 114 is scanned, the embedded data in the two-dimensional barcode 114 emulates user keystrokes and automatically enters the collection data, collection time, collector identifier, and any other data contained in the two-dimensional barcode 114 into the user interface.

Figure 8:
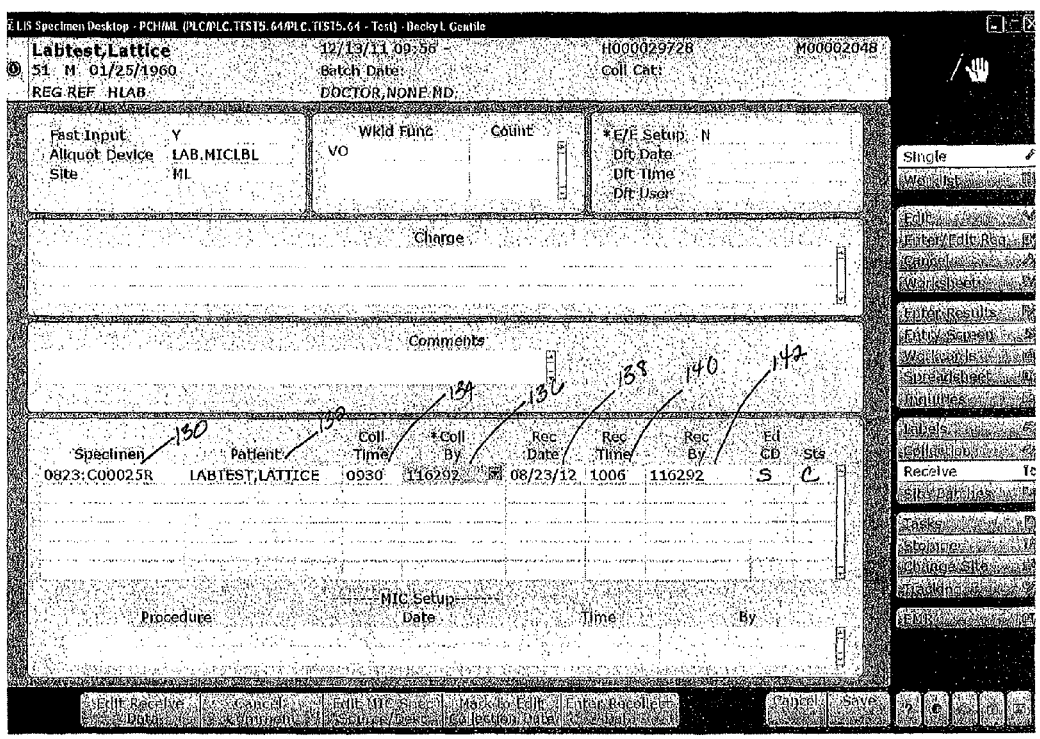
FIG. 8 is an illustrative user interface that may be populated by data contained in a two-dimensional barcode that is scanned during performance of the method steps of FIG. 4.
Figure 9:
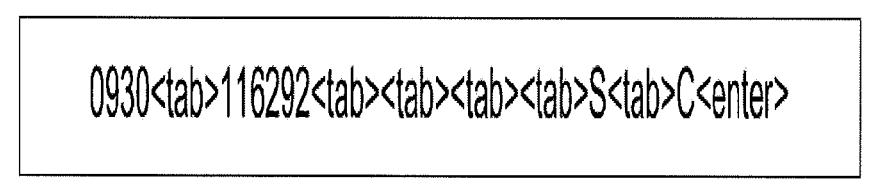

FIG. 8 depicts an illustrative user interface for use with the system and/or methods described herein. In an illustrative embodiment of data entry, when the linear barcode 110 is scanned, a specimen identification field 130 may be populated with the accession number. In an illustrative embodiment, a patient field 132 may be automatically populated with the patient name and the cursor may move to the next field, which is a collection time field 134. After scanning the linear barcode 110, the two-dimensional barcode 114 may be scanned, thereby beginning the data input depicted in FIG. 9. As depicted in FIG. 9, scanning of the two-dimensional barcode 114 would enter "0930" into the collection time field 134, tab to a collected by field 136, enter "116292" in the collected by field 136, tab to the received date field 138, tab to the received time field 140, tab to the received by field 142, tab to the Ed CD field 144, enter "S" in the Ed CD field 144, tab to the Sts field 146, enter "C" in the Sts field 146, and select "Enter" or "Return."

While one illustrative user interface is shown in FIG. 8 and one illustrative set of instructions encoded within a barcode is shown and described, any user interface or instructions may be utilized without departing from the scope of the present disclosure.

Figure 1:
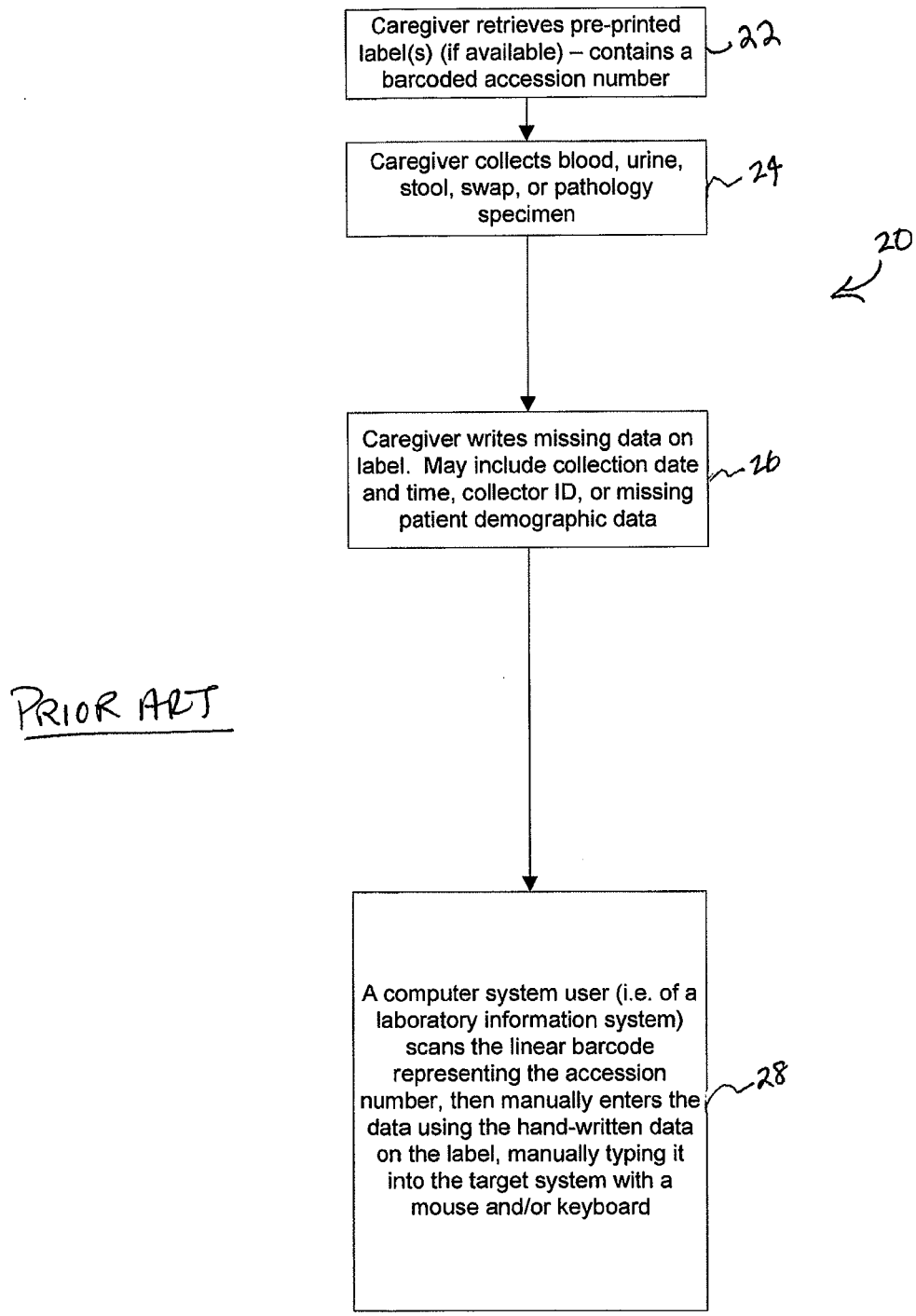
FIG. 1 is flow diagram depicting method steps taken during operation of a manual prior art system for specimen collection and inputting specimen information into a target system.
Figure 2:
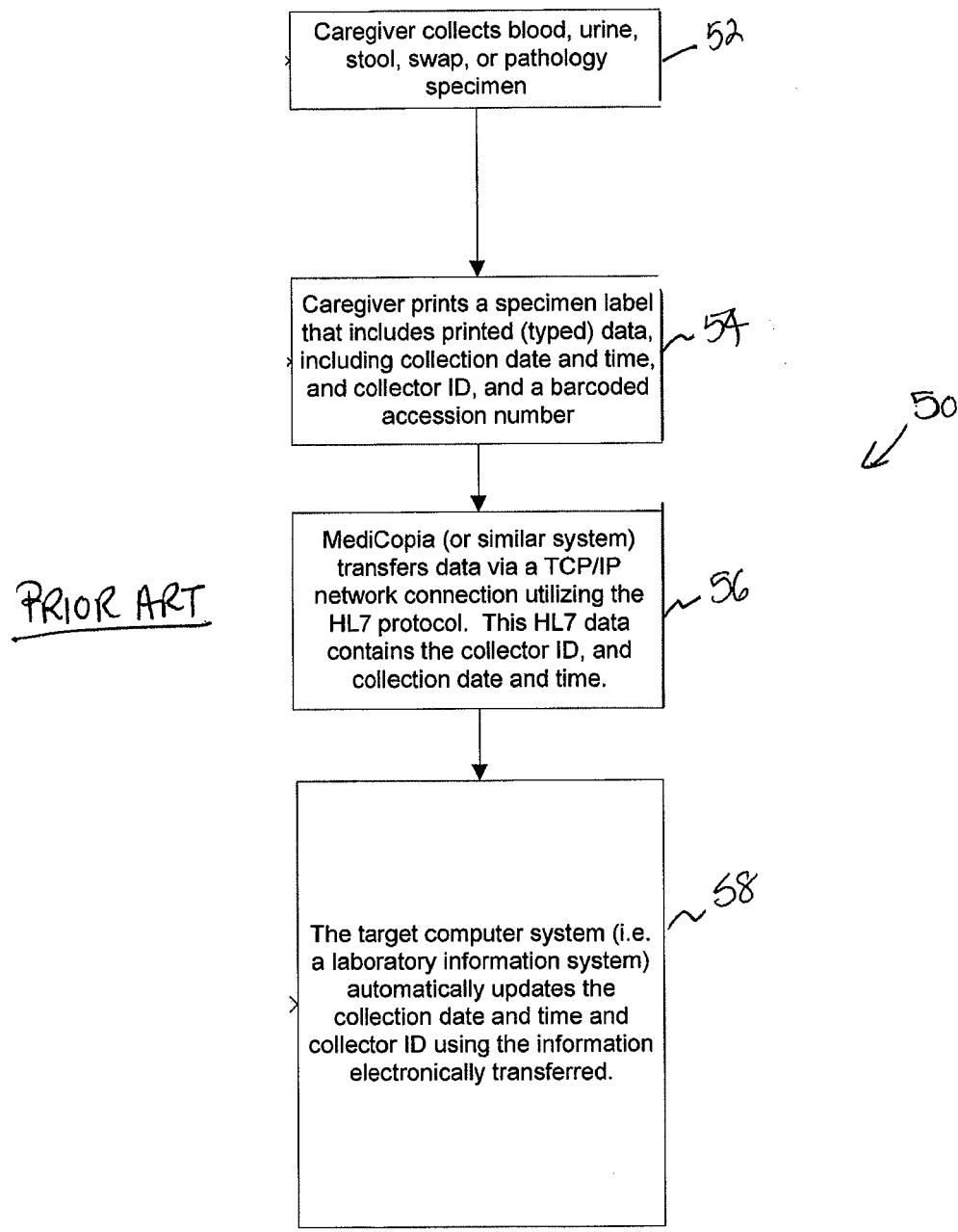
FIG. 2 is a flow diagram depicting method steps taken during operation of an electronic prior art system for specimen collection and inputting specimen information into a target system.

Once the data is entered in the user interface, the data is saved into a database within the target system. Automatic input of data from the barcode 114 increases productivity and reduces the potential for errors that might occur, for example, in the manual system described above with respect to FIG. 1.

After the data has been saved into the database within the target system, subsequent analysis equipment would only scan the linear barcode containing the accession number, using this primary identifier for analysis reporting. In this manner, once the two-dimensional barcode 114 is scanned, the two-dimensional barcode 114 need not be scanned in the same target system again. If a different target system is utilized, the two-dimensional barcode 114 must be scanned a single time for that target system.

While the two-dimensional barcodes 114 are depicted and described herein as being utilized for a label 106, for example, for a specimen container and for inputting data into a target system, the two-dimensional barcodes 114 described herein may be utilized in other medical or non-medical scenarios. In an illustrative embodiment, in medical or anatomical pathology, specimens often do not get assigned a unique specimen identifier (i.e., an accession number) until they reach the laboratory. In such scenarios, specimens are often accompanied by a handwritten multi-part form that has checkboxes and lines for manual entry of collection information and the pathological testing to be performed. The system described above with respect to the method of FIG. 4 may be used to generate specimen labels at the time of collection, wherein the labels contain a two-dimensional barcode similar to the barcode 114 of FIG. 7. Again, the two-dimensional barcode may represent data to be entered at the time of assigning a unique identification or accession number ("accessioning") by a laboratory information system, pathology information system, electronic health record, or other healthcare system. A full-size printout with multiple barcodes defining the pathology order and specimens may also be printed and later scanned during the accessioning process to reduce transcription errors.

In a further illustrative embodiment, two-dimensional barcodes 114 may be used for recording of information related to vitals. Nurses, doctors, or other healthcare professionals generally manually enter data into an electronic health record (EHR) of a patient because they measure and receive data from vitals measurement systems (e.g., a blood pressure cuff, thermometer, etc.) that do not provide an electronic interface to the EHR system. A two-dimensional barcode may be printed by one or more vitals measurement systems and read by a scanner associated with the EHR system. Each barcode may include multiple vitals measurements for automating transfer of data from either the vitals measurement or between computer systems.

While a single label 106 is depicted including the various forms of data, any number of labels may be utilized without departing from the present disclosure.

The systems and methods for inputting specimen information in a target system as disclosed herein may be utilized with respect to any biological, pathology, or other suitable specimen at any inpatient or outpatient location.

Any of the embodiments described herein may be modified to include any of the structures or methodologies disclosed in connection with other embodiments.

A method of inputting medical information comprises printing a two-dimensional barcode from a first system, wherein the barcode contains embedded data to input into a second system and wherein the data is separated by embedded key strokes that emulate entry of data into a user interface of the second system. The method further includes the steps of scanning the barcode utilizing a scanner associated with the second system and entering the embedded data into the user interface of the second system. The embedded key strokes may include tabs, enter keys, and function keys.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A method of inputting medical information, the method comprising the steps of:
    printing a two-dimensional barcode from a first system, wherein the two-dimensional barcode comprises embedded data to input into a second system and wherein the data is separated by embedded key strokes that emulate entry of data into a user interface associated with the second system, wherein the first system is not capable of transmitting the embedded data in the two-dimensional barcode via a network to the second system;
    scanning the two-dimensional barcode utilizing a scanner associated with the second system; and
    entering the embedded data into the user interface of the second system.

2. The method of claim 1, wherein the embedded key strokes include at least one of a tab, an enter key, a function key, a number, a character, and a space.

3. The method of claim 1, further including the step of attaching the two-dimensional barcode to a container holding a specimen for tracking, wherein the step of attaching occurs after printing the two-dimensional barcode and prior to scanning the two-dimensional barcode.

4. The method of claim 1, further including the step of saving embedded data in a database within a record associated with the unique identifier, wherein the database is associated with the second system.

5. The method of claim 1, further including the step of inputting data related to a collected specimen into a user device associated with the first system prior to printing the two-dimensional barcode.

6. The method of claim 5, further including the step of storing at least some of the data in a database associated with the user device.

7. A method of inputting medical information, the method comprising the steps of:
   printing a two-dimensional barcode from data contained within a first database of a first system, wherein the two-dimensional barcode comprises embedded data to input into a user interface and a second database of a second system and wherein the data is separated by embedded key strokes that emulate entry of data into the user interface associated with the second system and further wherein the embedded data comprises information related to an item to be tracked;
   scanning the two-dimensional barcode utilizing a scanner associated with the second system; and
   entering the embedded data into the user interface and the second database of the second system;
   wherein the second database is different from and not associated with the first database.

8. The method of claim 7, further including the step of populating the user interface with the unique identifier and any information associated with the unique identifier after scanning the linear barcode.

9. The method of claim 8, further including the step of saving the unique identifier in a database and associating the unique identifier with a record, wherein the database is associated with the second system.

10. The method of claim 9, further including the step of saving the embedded data in the database within the record associated with the unique identifier.

11. The method of claim 7, wherein the embedded key strokes include at least one of tabs, enter keys, and function keys.

12. The method of claim 7, wherein the item is a container holding a specimen taken from a patient for analysis.

13. The method of claim 7, further including the step of inputting data related to a collected specimen into a user device associated with the first system prior to printing the linear or two-dimensional barcodes.

14. The method of claim 13, further including the step of storing at least some of the data in a database associated with the user device.

15. The method of claim 7, further including the steps of:
   printing a linear barcode from a first system, wherein the linear barcode comprises a unique identifier for an item to be tracked; and
   scanning the linear barcode utilizing a scanner associated with the second system.

16. A system for inputting medical information, comprising:
   a user device associated with a first system, wherein the user device is configured to accept data and input the data in a first database associated with the first system;
   a printer associated with the user device for printing a linear barcode comprising a unique identifier for an item to be tracked and a two-dimensional barcode, wherein the two-dimensional barcode comprises embedded data to input into a second system that is not connected or networked with the first system for the purpose of transmitting the embedded data in the two-dimensional barcode and wherein the data is separated by embedded key strokes that emulate entry of data into a user interface associated with the second system and further wherein the embedded data comprises information related to the item to be tracked; and
   wherein the second system includes a scanner for scanning the linear and two-dimensional barcodes and populating information associated with the linear and two-dimensional barcodes into the user interface associated with the second system and further saving the information in a second database associated with the second system, wherein the second database is not the same as or associated with the first database of the first system.

17. The system of claim 16, further including a database associated with the first system for storing data accepted by the user device.

18. The system of claim 16, further including a database associated with the second system for storing data populated within the user interface.

19. The system of claim 16, wherein the embedded key strokes include at least one of a tab, an enter key, a function key, a number, a character, and a space.

* * * * *